(12) United States Patent
Kadziauskas et al.

(10) Patent No.: US 6,699,212 B1
(45) Date of Patent: *Mar. 2, 2004

(54) PHACO THERMAL CONTROL APPARATUS AND METHOD

(75) Inventors: Kenneth E. Kadziauskas, Las Flores, CA (US); Paul W. Rockley, Laguna Niguel, CA (US)

(73) Assignee: Advanced Medical Optics, Santa Ana, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 09/599,127

(22) Filed: Jun. 22, 2000

Related U.S. Application Data

(63) Continuation-in-part of application No. 09/037,638, filed on Mar. 10, 1998, now Pat. No. 6,083,193.

(51) Int. Cl.⁷ .................... A61B 17/20; A61M 1/00; A61F 9/00
(52) U.S. Cl. .................. 604/22; 604/28; 604/35; 606/107
(58) Field of Search .............. 604/19, 22, 27, 604/28, 31, 35, 39, 40, 43, 44, 65–67, 118; 606/107, 159, 167–71; 601/2, 52

(56) References Cited

U.S. PATENT DOCUMENTS

| | | | | |
|---|---|---|---|---|
| 4,156,187 A | | 5/1979 | Murry et al. ............. 324/142 |
| 5,279,547 A | * | 1/1994 | Costin .................. 604/22 |
| 5,700,240 A | * | 12/1997 | Barwick et al. ........... 604/22 |
| 6,083,193 A | * | 7/2000 | Kadziauskas et al. ....... 604/22 |
| 6,193,683 B1 | * | 2/2001 | Ludin et al. ............. 604/22 |
| 6,261,297 B1 | * | 7/2001 | Kadziauskas et al. ...... 606/107 |
| 6,315,755 B1 | * | 11/2001 | Sussman ................ 604/28 |

FOREIGN PATENT DOCUMENTS

| | | | |
|---|---|---|---|
| WO | WO 92/07622 | 5/1992 | ......... A61N/5/02 |
| WO | WO 99/45868 | 9/1999 | ......... A61F/9/007 |

* cited by examiner

*Primary Examiner*—Patricia Bianco
(74) *Attorney, Agent, or Firm*—Walter A. Hackler; Peter Jon Gluck

(57) ABSTRACT

Control apparatus for an ultrasonic phacoemulsification handpiece utilizes flow rates and temperature measurements as well as power provided to a handpiece for calculating a matrix of power level duty cycle combination that would not generate sufficient heat to create a burn in eye tissue and either prevent operation of handpiece in the matrix or alert a surgeon of such use.

6 Claims, 2 Drawing Sheets

PHACO THERMAL CONTROL APPARATUS AND METHOD

Figure 1:
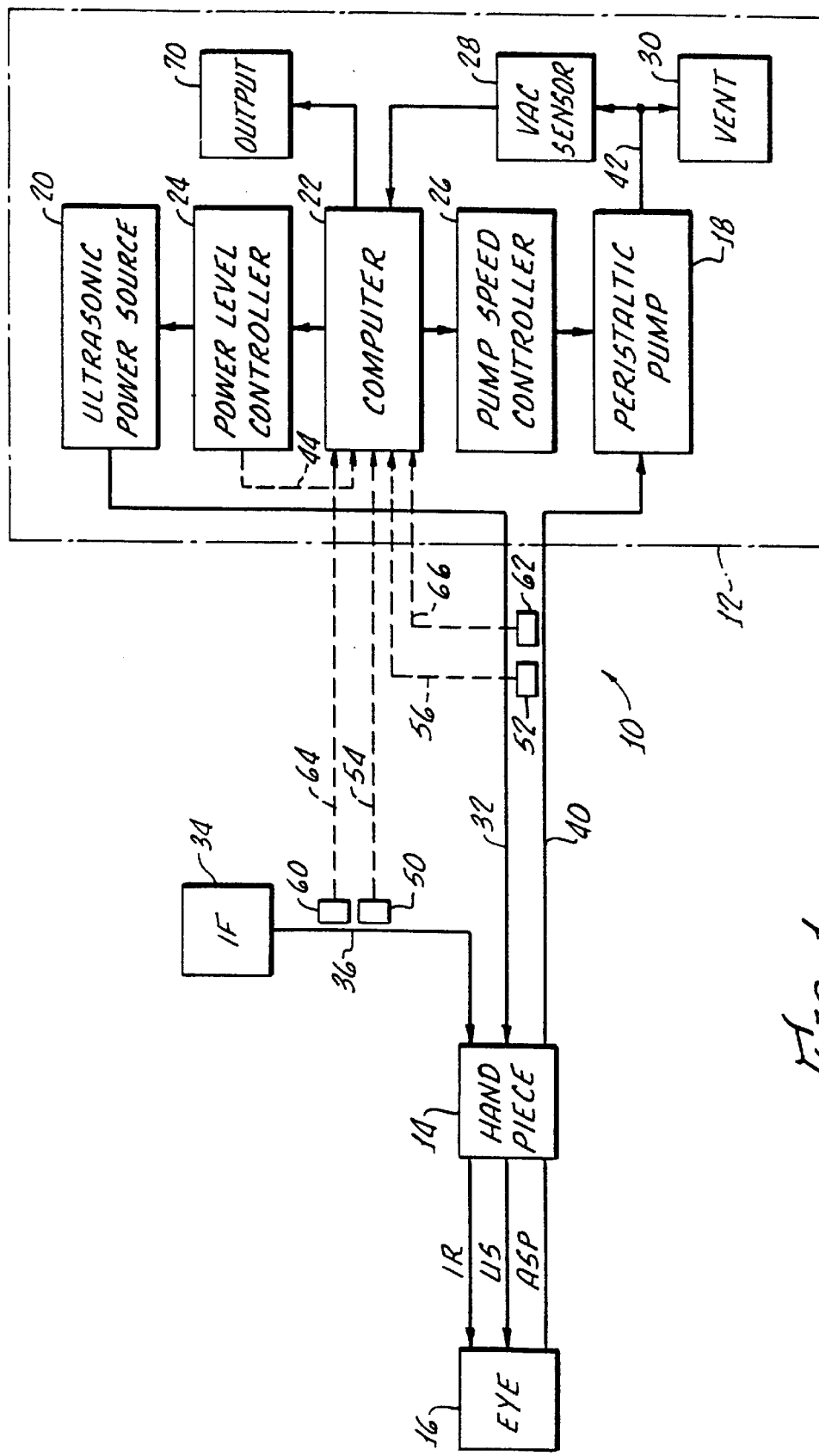

The present application is a continuation-in-part of U.S. Ser. No. 09/037,638 filed Mar. 10, 1998 now U.S. Pat. No. 6,083, 193.

The present invention is generally directed to apparatus and a method for controlling power delivery to an ultrasonic phacoemulsification handpiece as well as controlling fluid flow to and from an eye during ocular surgery with the phacoemulsification handpiece. More particularly, the invention is directed to apparatus and a method for controlling phaco power delivery and/or fluid flow based upon the amount of thermal energy delivered to an eye over a specific period of time.

Phacoemulsification of cataracts lenses is a medically recognized technique. The method generally includes making of a corneal incision and the insertion of a hand held surgical implement, i.e., handpiece, which includes a needle which is ultrasonically driven in order to emulsify the eye lens. Simultaneously, with this emulsified lens and a vacuum provided for aspiration of the emulsified lens and inserted fluids.

In order to maintain normal pressure within the eye, a balanced salt solution is provided as an irrigation fluid and typically supplied from an elevated chamber. Importantly, the irrigation and aspiration of fluid through the eye must be carefully monitored in order to maintain normal pressure within the eye during surgical procedures. For example, an underpressure condition may cause distortion of the eye which often may interfere with surgical procedures. On the other hand, overpressure may cause damage to the eye.

As hereinabove noted, pressure in the eye may be controlled by physical elevation of the source of irrigation fluid interconnected to the phacoemulsification handpiece. Aspiration of fluid is typically controlled through the use of peristaltic pump or the like.

It should be appreciated that the control of irrigation and aspiration fluids is a dynamic problem. For example, during surgical procedures, fragments of broken tissue may temporarily block an aspiration line or the handpiece. This may lead to a differential pressure which is typically accommodated by stopping or slowing aspiration flow through the regulation of the peristaltic pump connected to the aspiration line.

During aspiration of the lens and aspiration fluid, particles may restrict the aspiration flow from the eye through an aspiration port in the tip of the phacoemulsification handpiece. In order to clear this occlusion, vacuum levels may be increased to create a greater differential pressure across the occluding particle in an effort to move the particle downstream and away from the eye. Typically, particles require much higher force to start movement than it takes to continue movement of the particle to the peristaltic pump. Once a particle moves, it creates a subsequent volume of fluid to take up the space it once occupied. This volume may be momentarily larger than the volume of fluid in the eye, therefore, producing a momentary-dimpling of the eye.

It has been shown that the pressure sensing of this condition is well within the operation of the phaco machine.

However, of further consideration regarding the utilization of phacoemulsification handpiece, is the amount of power delivered to the lens by the handpiece in order to fragment the lens. If too much power is delivered to the handpiece, without concomitant fluid or cooling irrigation fluid, local temperatures of the eye may rise to a level causing localized trauma. On the hand, the entire eye may be heated during the procedure within the anterior chamber which may cause damage. Thus, it is important to not only control the power delivery of a phacoemulsification handpiece, but to provide a means for calculating elevated anterior chamber temperatures in order to prevent any tissue damage due to excess delivered power. Such damage can occur within one to two seconds under adverse heating conditions.

It should be appreciated that in combination with the occlusion of the phacoemulsification needle, as hereinabove described, the fluid flowing from the eye can vary considerably. Thus, heat is not removed from the eye in a generally continuous basis, but, of course, is dependent upon the actual fluid flow as a function of time. Heretofore, consoles for providing irrigation fluid and power of an ultrasonic phacoemulsification handpiece and aspirating fluid from the eye during ocular surgery, have not taken into account energy and power considerations nor utilized same for controlling the operation of the phacoemulsification handpiece.

In addition, prior art devices have not provided any warning to surgeon as to impending damage, i.e., burning, to an eye which can be caused by overheating.

The present apparatus and method provide for such operation.

SUMMARY OF THE INVENTION

Control apparatus, by itself, or for use in a control console for providing irrigation fluid and controlling power to an ultrasonic phacoemulsification, or cataract extraction, handpiece and aspiration from an eye during ocular surgery, generally includes a means for monitoring energy provided to the handpiece and means for monitoring energy removed from the eye by aspirated fluid. In connection therewith, a computer responsive to input from the means for monitoring power provided and removed, provides a means for calculating an energy balance over a time interval and determining a matrix of power levels and duty cycle combination that will not generate sufficient heat to create a burn of eye tissue. The power may then be regulated in accordance with the matrix.

In addition, regulation of the fluid flow may also be performed in response to the matrix calculation.

More particularly, the means for monitoring power removed from the eye may include a means for measuring the flow rate of the aspirated fluid and/or irrigation fluid and may further include a means for measuring a temperature difference between the irrigation fluid and the aspirated fluid.

Additionally, output means, which is responsive to the computer means, may provide an indication of eye temperature based upon the energy balance. Specifically, the output means may provide an alarm at a selected eye temperature level. This enables a continuous monitoring of the eye temperature and, in addition, either visual or audible alarm, may be provided at any selected level in order to attract attention to an energy imbalance in order to prevent thermal damage to eye tissue.

Correspondingly, a method for regulating fluid flow and power to an ultrasonic phacoemulsification, or cataract extraction, handpiece, includes the steps of monitoring power provided to the handpiece, monitoring power removed from the eye by the aspirated fluid and calculating, in response to input from the steps of monitoring the power provided and the power removed, a matrix of power levels and duty cycle combinations that will not generate sufficient heat to create a burn in eye tissue. The matrix can then be used to prevent operation of the handpiece outside the matrix or alert a surgeon of potential burns if the handpiece is operated outside the matrix.

Alternately, a test handpiece can be used to determine the matrix and subsequently used handpiece can be prevented from operation outside the matrix or a warning can be given to a surgeon when a handpiece is used outside the matrix.

DETAILED DESCRIPTION

Figure 2:
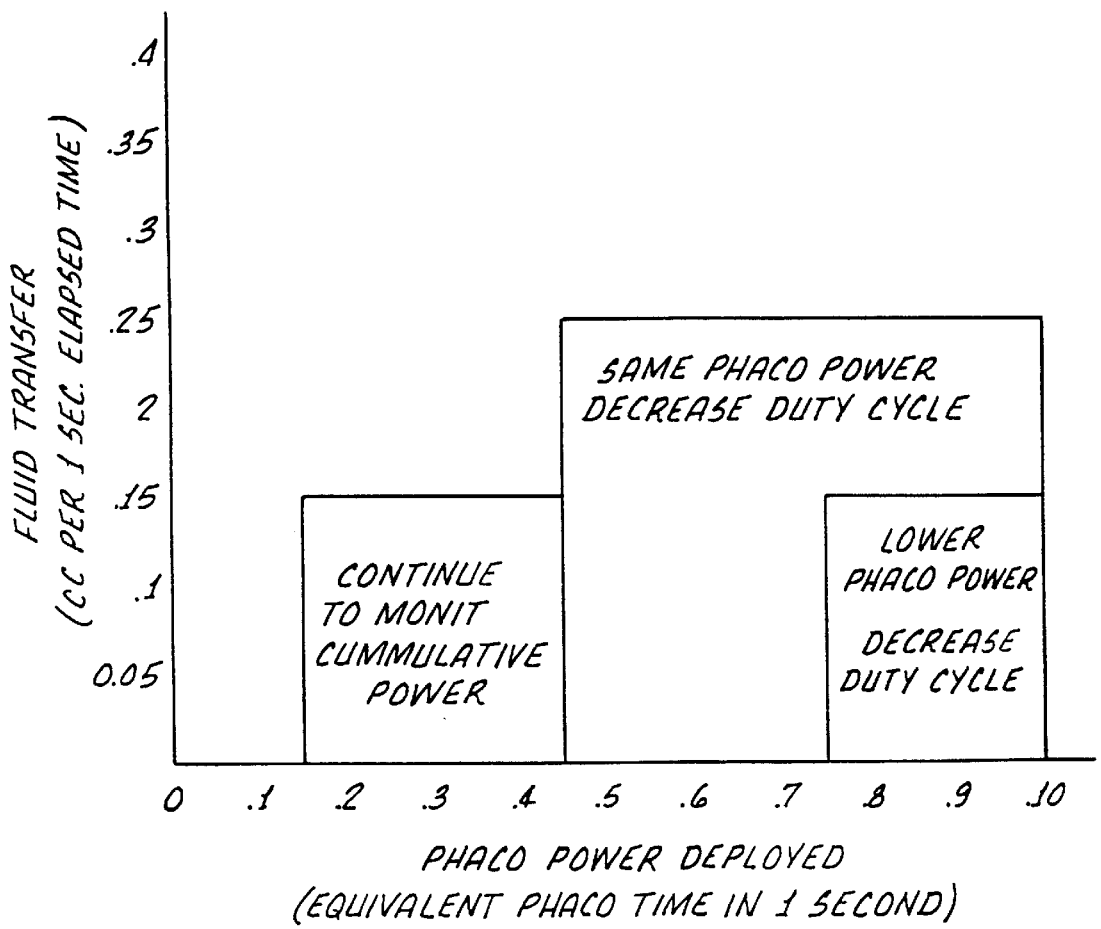

The advantages and features of the present invention will be better understood by the following description, when considered in conjunction with the accompanying drawings, in which:

FIG. 1 is a block diagram of control apparatus in accordance with the present invention; and FIG. 2 is a plot of fluid transfer as a function of Phaco power displayed during a phacoemulsification procedure.

Turning now to FIG. 1, there is shown, in functional block diagram form, a phacoemulsification system. The system 10 includes a control console 12 for providing irrigation fluid and power to an ultrasonic phacoemulsification handpiece 14, and aspiration fluid from an eye 16 during ocular surgery. The console 12 includes a variable speed peristaltic pump 18 which provides a vacuum source, a source of pulsed ultrasonic powers 20, and a microprocessor computer 22, an ultrasonic power level controller 24 and a pump speed controller 26. A vacuum sensor 28 provides input to the computer 22 representing a vacuum level on an input side of the peristaltic pump 18. Suitable venting is provided by vent 30. This apparatus and availability is described in greater detail in U.S. Pat. No. 5,700,240 which is incorporated herewith in its entirety for describing a control console 12 suitable for use in the present invention.

The console 12 supplies ultrasonic power on line 32 to the handpiece 14 and an irrigation of fluid source 34 is coupled to the handpiece 14 through line 36. The irrigation fluid and ultrasonic power applied by the handpiece 14 to a patient's eye, which is indicated diagrammatically by block 16. Aspiration of the eye 16 is achieved through line 40.

The power level controller 24 provides a means from monitoring power provided to the handpiece 14 by the console 12 and an output indicating a signal corresponding to the power provided to the handpiece 14 may be separately imputed to the computer 22 as indicated by the dashed line 44.

Any suitable temperature sensors 50, 52 connected to the computer 22 by lines 54, 56 and flow sensors 60, 62 interconnected to the computer by lines 64, 66, respectively, provide a means for monitoring power removed from the eye 16 by aspirated fluid. The temperature sensors 50, 52 and flow sensors 60, 62 may be of any suitable type. Since the flow rates and temperature of the aspiration and irrigation fluids are known, as well as the power provided to the handpiece, an energy balance can be calculated by the computer.

Energy balance, as the term is used herein, assumes flow through the handpiece which is not chemically changed, i.e., no chemical reaction of the fluid occurs within the eye 16 or the handpiece 14.

The microprocessor computer 22 accordingly is capable of determining cumulative phaco power delivered over a period of time as well as the cumulative fluid removed from the eye by the peristaltic pump 16. Under the further assumption of a tight wound and minimal fluid leakage, aspiration flow and irrigation fluid are equivalent in the eye system. Therefore, a correlation is established between the fluid flow, phaco power and heat generation in the handpiece 14. In fact, empirically, the flow rate of irrigation/aspiration fluids may be utilized to determine the eye temperature given the heat input by the phaco power provided by the handpiece. In this instance, the fluid temperatures need not be continually measured or monitored.

As hereinabove noted, decreasing flow coupled with phaco power deployment over extended time may result in burns or chamber heating.

The computer 22 utilizes either a look-up table or algorithm to determine an energy balance and whether the control console 12 should continue with existing power and fluid settings or switch to modified settings which may be preprogrammed by a user. In addition, the computer may modulate the phaco power level or duty cycle based upon the level of a "heat factor" determined by the energy balance.

In addition, the computer 22 may provide an output indicated by the block 70, which may be of an suitable output device or alarm, for providing an indication of high temperature based on the energy balance.

An example of a heat factor determination with corresponding system response is shown in FIG. 2, which represents an algorithm for handpiece 14 operation.

Several methods may be utilized to determine the heat factor inducing mathematical algorithm or a look-up table contained within system memory. FIG. 2 illustrates one way in which a heat factor may be determined from a two dimensional matrix. FIG. 2 also demonstrates one example of how a system may be programmed to respond based upon the determined heat factor within this two dimensional matrix.

A combination of change in phaco power as well as duty cycle is shown as a response to ultrasonic power and fluid transfer within a given increment of time. By monitoring the fluid removed from the eye by the aspiration means utilizing a microprocessor, the quantity of fluid capable of transferring heat away from the eye in a given increment of time can be determined or approximated. In addition, the system 10 is also capable of monitoring the cumulative ultrasonic energy deployed into the eye 16 in a given increment of time by utilizing a microprocessor 22 to either calculate energy directly from the power level utilized by the surgeon via footpedal control, not shown, or by monitoring equivalent phaco time. Equivalent phaco time is the average percent power setting on the system used by the surgeon divided by 100. Heat generation within the eye 16 is a function of the energy deployed. In response to these two calculations, a coordinate is determined with the two dimensional matrix. The system 10 response to this coordinate is either provided pre-programmed into the system or determined by the surgeon and programmed and/or modified in either a pre-operative or inter-operative manner.

The equivalent time set for the in FIG. 2 corresponds to full duty cycle of one second. That is, if the handpiece 14 is powered at one-half duty cycle, then the active time would be 2 sec., corresponding to an equivalent time of 1 sec. Full duty cycle.

As hereinbefore noted, the computer 22 may be also programmed to calculate, or determine, a matrix of power level vs duty cycle combination that will not generate sufficient heat to create a burn of eye tissue and either prevent operation of the handpiece 14 in the matrix or alert a surgeon of such use.

A test handpiece (not shown) may be used in the method of the present invention to determine the matrix and subsequent handpieces or systems either prevented from operating outside the matrix or providing a warning to a surgeon when the handpiece or system is operating outside the matrix.

Although there has been hereinabove described controlled apparatus in accordance with the present invention, for the purpose of illustrating the manner in which the invention is used to advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. A method for regulating fluid flow and energy in a control console for providing irrigation fluid and energy to an ultrasonic phacoemulsification handpiece and aspirating fluid from an eye during ocular surgery, the method comprising the steps of:

monitoring energy provided to the handpiece;

monitoring energy removed from the eye by aspirated fluid including measuring a flow rate of aspiration fluid and measuring a temperature difference between the irrigation fluid and the aspiration fluid; and calculating, in response to input from the steps of monitoring energy provided and energy removed, a matrix of power levels and duty cycle combinations that will not generate sufficient heat to create damage of eye tissue.

2. The method according to claim 1 further comprises the step of preventing operation of the handpiece at power levels and duty cycle combinations outside of the calculated matrix.

3. A method for regulating fluid flow and energy in a control console for providing irrigation fluid and energy to an cataract extraction handpiece and aspirating fluid from an eye during ocular surgery, the method comprising the steps of:

monitoring energy provided to a test handpiece;

monitoring energy removed from the eye by fluid aspirated by the test handpiece including measuring a flow rate of aspiration fluid and measuring a temperature difference between the irrigation fluid and the aspiration fluid using the test handpiece;

calculating, in response to input from the steps of monitoring energy provided and energy removed by the test handpiece, a matrix of power levels and duty cycle combinations that will not generate sufficient heat to create damage in eye tissue;

using the matrix in subsequent handpiece systems to prevent operation of the subsequent handpiece systems outside the matrix of power levels and duty cycle.

4. A method of regulating fluid flow and energy in a control console for providing irrigation fluid and energy to an ultrasonic phacoemulsification handpiece and aspirating fluid from an eye during ocular surgery, the method comprising the steps of:

monitoring energy provided to a test handpiece;

monitoring energy removed from the eye by fluid aspirated by the test handpiece including measuring a flow rate of aspiration fluid and measuring a temperature difference between the irrigation fluid and the aspiration fluid using the test handpiece;

calculating, in response to input from the steps of monitoring energy provided and energy removed by the test handpiece, a matrix of power levels and duty cycle combination that will not generate sufficient heat to create damage in eye tissue;

using the matrix in order to alert a user of subsequent handpiece systems of selected power levels and duty cycle that would cause damage of eye tissue.

5. A method for regulating fluid flow and energy in a control console for providing irrigation fluid and energy to an ultrasonic phacoemulsification handpiece and aspirating fluid from an eye during ocular surgery, the method comprising the steps of:

using a test handpiece to determine a matrix of power levels and duty cycle combinations that will not generate sufficient heat to create damage in eye tissue; and using the matrix in subsequent handpiece systems to prevent operation of the subsequent handpiece systems outside the matrix of power levels and duty cycle.

6. A method for regulating fluid flow and energy in a control console for providing irrigation fluid and energy to an cataract extraction handpiece and aspirating fluid from an eye during ocular surgery, the method comprising the steps of:

using a test handpiece to determine a matrix of power levels and duty cycle combinations that will not generate sufficient heat to create damage in eye tissue; and using the matrix in order to alert a user of subsequent handpiece systems of selected power levels and duty cycles that would cause damage of eye tissue.

* * * * *